Figure 1:
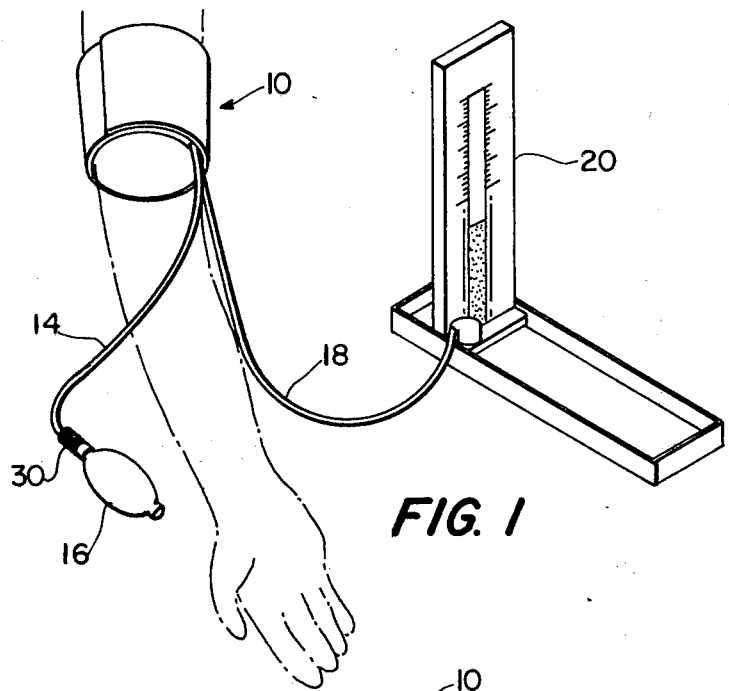

United States Patent [19]

Howell

[11] 4,142,518

[45] Mar. 6, 1979

[54] SPHYGMOMANOMETER PRESSURE RELEASING MEANS

[76] Inventor: William L. Howell, 3615 Macomb St., NW., Washington, D.C. 20008

[21] Appl. No.: 785,218

[22] Filed: Apr. 6, 1977

[51] Int. Cl.² ............................................. A61B 5/02
[52] U.S. Cl. ............................ 128/2.05 G; 251/342
[58] Field of Search ............... 128/2.05 A, 2.05 G, 128/2.05 M, 2.05 Q, 2.05 R, 274, 327; 251/342

[56] References Cited

U.S. PATENT DOCUMENTS

| | | | |
|---|---|---|---|
| 2,761,593 | 9/1956 | Spiess, Jr et al. | 251/342 |
| 3,504,663 | 4/1970 | Edwards | 128/2.05 G |
| 3,656,512 | 4/1972 | Countryman | 251/342 |
| 3,699,964 | 10/1972 | Ericson | 128/274 |
| 3,779,236 | 12/1973 | Stewart | 128/2.05 G |

*Primary Examiner*—William E. Kamm
*Attorney, Agent, or Firm*—J. Harold Kilcoyne

[57] ABSTRACT

A sphygmomanometer pressure release means, i.e. a means for releasing the pressure in the pneumatic cuff thereof by simple bending pressure applied to the tubing extending from the "squeeze" bulb to the pneumatic cuff and at a point along the tubing adjacent the squeeze bulb.

5 Claims, 5 Drawing Figures

U.S. Patent     Mar. 6, 1979     4,142,518

SPHYGMOMANOMETER PRESSURE RELEASING MEANS

This invention relates to improvements in means for releasing the pressure in the pneumatic cuffs of sphygmomanometers used in the measuring of a person's blood pressure.

BACKGROUND OF THE INVENTION

Present means for the release of pressure in sphygmomanometer cuffs conventionally take the form of a manually operable pressure release valve located in the tubing line between the "squeeze" bulb and the cuff at a point therealong just in advance of said squeeze bulb. Unfortunately, such valves are subject to wear and when worn result in jerky cuff deflation, making blood pressure estimations both difficult and inaccurate. Indeed, as many as 20% of a hospital's sphygmomanometers may be so disabled and/or out at one time for repair of the worn valve, which fact points to the need of a pressure release means which is not subject to wear and which at the same time makes deflation of the pneumatic cuff possible of attainment.

To assist in an appreciation of this need, the following brief description of the instruments now in use for and how blood pressure is taken therewith follows;

These instruments consists of a wrap-around cuff incorporating a pneumatically inflatable bag. Two tubes are connected to said inflatable bag, one extending to a squeeze bulb used for inflation of said bag, and the other extending to a manometer, i.e. a pressure indicating device which may consists of a mercury-column type manometer or a spring-type manometer.

The aforesaid squeeze bulb, which is provided at its opposite ends with a one-way air inlet valve and with a one-way outlet valve, respectively, is normally maintained distened by virtue of its configuration and the form-sustaining material, usually rubber, from which it is fashioned. However when squeezed, air pressure within the bulb is increased to a degree closing its one-way air inlet valve and opening its one-way outlet valve thereby forcing air into the tubing line extending to the pneumatic cuff and when squeeze pressure on the bulb is released, the bulb reforms, air being thereby drawn into its interior via the one-way air inlet valve.

Conventionally, air pressure in the tubing line and in the bag component of the pneumatic cuff may be lowered by means of the manually operable screw-type valve which is subject to wear, as previously noted.

In taking ones blood pressure by use of an instrument as foresaid, the pneumatic cuff is wrapped around the patient's arm (between elbow and shoulder) and air is pumped into the inflatable bag component thereof by squeeze pressure applied to the bulb, thereby raising the mercury column to 200-250 mm (such assuming a mercury manometer is used), with the result that the artery is compressed to a degree that blood flow beyond the cuff does not occur and the distal portion of the artery is collapsed.

The manually operable screw-valve which up to this point of the procedure has been closed to prevent the escape of air is now opened slightly to allow pressure in cuff to fall.

When the pressure in the cuff is lowered to a certain point— the pressure in the artery resulting from contraction of the heart begins to cause "squirts" of blood to escape under the cuff to the distal collapsed artery. This produces a sound with each squirt which is heard with a stethoscope placed over the collapsed artery, such sounds being known as Korotcoff sounds, named for the physician who first described them.

At the pressure point at which these sounds come through with each heart beat — the systalic blood pressure, i.e., the highest pressure which results from contraction of the heart, is recorded.

Even when the heart is at rest, however, pressure is maintained in the arteries. Such pressure, termed the diastalic pressure, is determined as follows;

Air pressure in the inflatable bag is gradually reduced by allowing air to escape via the screw valve. During this release of pressure, blood continues to squirt from under the cuff into the distal artery producing Korotcoff sounds. When, however, pressure is lowered sufficiently, blood-flow beneath the cuff becomes continuous and the Korotcoff sounds become muffled or disappear, the pressure at this point as registered on the manometer being the patient's diastalic pressure.

From the foregoing, the importance and indeed the crying need of and for a means for releasing the pressure in sphygmomanometer cuffs smoothly and with uniformly predictable results not possible of attainment with presently used pressure release valves employed for this purpose because they are subject to wear and/or being otherwise disabled, becomes apparent, and it is a major object of the present invention to provide pressure release means of simple construction which is capable of effecting smooth deflation of said cuffs as needed, and in addition fulfills the additional objectives of inexpensive manufacture, longer useful life, simplicity of operation and ability to be packed in a smaller case than sphygmomanometers equipped with a screw valve in the tubing line to the cuffs as heretofore conventionally used for deflating said cuffs as needed.

Figure 2:
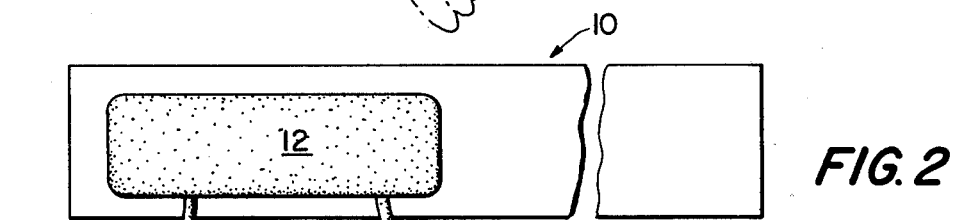
Figure 3:
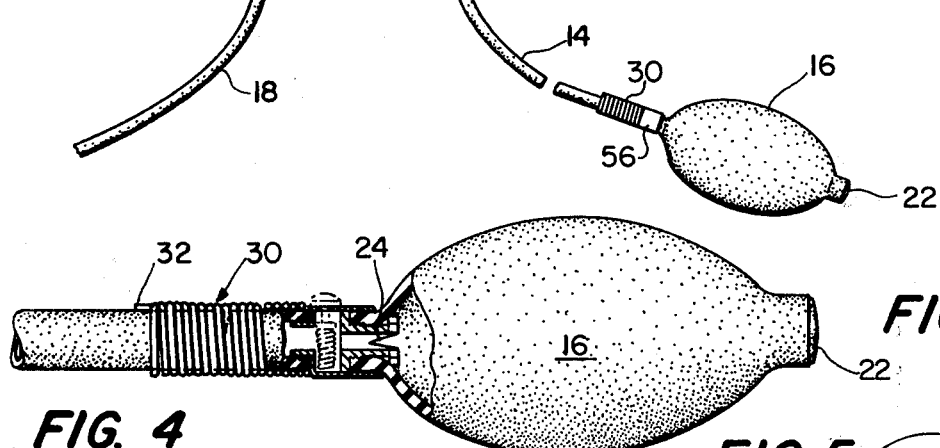
Figures 4, 5:
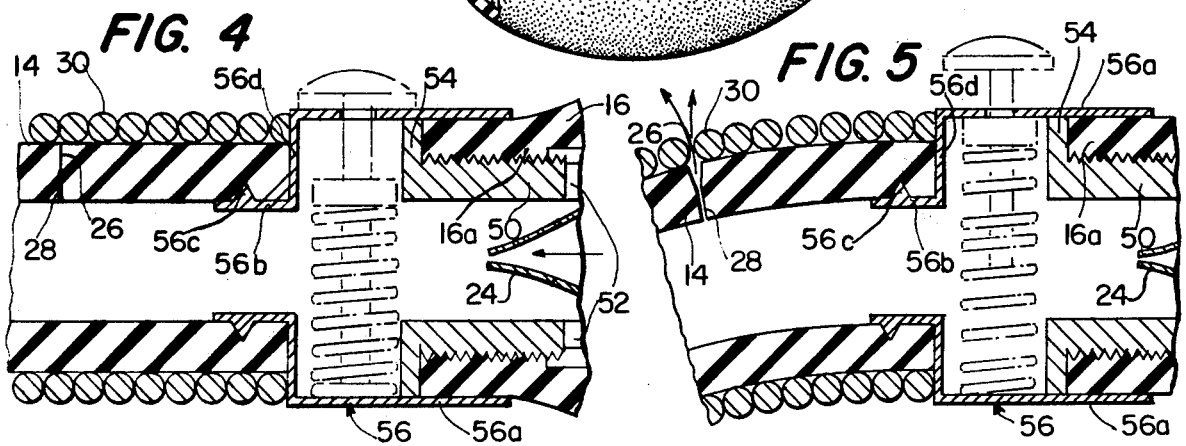

The above objects of the invention are attained by the simple, improved pressure release means illustrated in the accompanying drawing views, wherein FIG. 1 is a perspective view generally illustrative of a sphygmomanometer in use or about to be used to take a patient's blood pressure;

FIG. 2 is a view looking onto the pneumatic bag incorporated in the wrap-around cuff thereof and which taken together are hereinafter termed the "pneumatic cuff";

FIG. 3 is a side elevation partly in section, of the so-called squeeze bulb thereof, the connector interposed between said bulb and the tubing line, and a short length portion of the said tubing immediately distal of said bulb and which extends therefrom to the pneumatic cuff, which length portion incorporates the herein invention, i.e. the improved, simplified means for effecting the smooth and sure deflation of the pneumatic cuff as needed, by release of the pressure in the tubing line extending thereto;

FIG. 4 is an enlarged section of the aforesaid length portion of the tubing, which illustrates the connections between said tubing and said connector and between the connector and the squeeze bulb end, in which latter is mounted the one-way air outlet valve; and FIG. 5 is a view similar to FIG. 4, but which additionally shows the pressure release means according to the invention as having been activated by simple bending of the tubing, as by thumb pressure applied against the tubing outer surface slightly beyond said means.

Referring now to the aforesaid drawing figures in detail, reference numeral 10 (FIGS. 1 and 2) designates a conventional wrap-around cuff incorporating within its structure an inflatable bag 12 and forming therewith the "pneumatic cuff". To the bag of said pneumatic cuff are connected two tubing lines, the one designated 14 extending to and being connected to an air pressure generating means, i.e. a conventional squeeze bulb 16, and the second designated 18 going to a blood pressure indicating and/or recording device 20, illustratively a mercury manometer but which may also take the form of a spring-type manometer.

The aforesaid squeeze bulb 16 is preferably fashioned from rubber, although it may be made from any other deformable-reformable material suitable to serve as a squeeze bulb, and it is as usual provided at its opposite ends with a one-way air inlet valve 22 and a one-way air outlet valve 24, respectively, no detailed description of their construction being here given as such is conventional. Suffice it to say that the bulb normally assumes its "squeeze readiness" configuration, but when squeezed by the hand, air pressure is generated in its interior space, such closing the one-way air inlet valve 22 and causing the one-way air outlet valve 24 to open, whereupon air under pressure is forced through the tubing line 14 and thence to the pneumatic cuff 10-12, all as yields an indication and/or recording of a patient's blood pressure on the mercury column-type or the spring-type manometer 20, (whichever it employed) such assuming that said cuff is suitably placed on i.e. wrapped about, the patient's arm between elbow and shoulder.

Before describing in detail the improved pressure releasing means according to the invention, a brief description of the cylindrical sleeveform connector which is interposed between the air-outlet end of the squeeze bulb 16 and the proximal end of the tubing 14, as well as of the connections between said air-outlet end of the bulb and said connector and between said tubing end and the connector, would appear to be in order. More particularly and referring to FIGS. 4 and 5, it will be seen that the squeeze bulb 16 has a reduced neck end 16a which is secured about a tubular fitting 50 extending thereinto, and which is shown to be externally threaded with the threads being tightly engaged in (i.e. sinking into) the interior wall surface of said neck-end 16a for an appreciable length thereof. A nut 52 threaded on to the neck end of said fitting 50 serves the function of maintaining in fixed position the neck end 16a of the bulb between itself and a radially outwardly projecting flange 54 on the distal end of said fitting 50.

FIG. 4 also shows that a sleeve-form connector 56 is provided, such having a bulb-end portion 56a which extends about and has internal diameter such that its said end portion grips the aforesaid neck end 16a of the bulb 16 between its inner surface and the outer externally threaded surface of the fitting 50. The internal diameter of said connector end portion 56a is further such as to extend with but slight clearance over the aforesaid radially projecting fitting flange 54.

The tubing-connected end of the connector 56, i.e. the end thereof which makes connection with the tubing 14, terminates in a reduced diameter, axially extending neck 56b having external diameter slightly greater than the diameter of the tubing bore, and which further is provided on its external surface with a projecting tubing-gripping tooth 56c. Thus, upon the tubing end being forcibly pushed onto the extending neck 56b of the connector for a distance such that its end abuts the outer surface of the connector wall 56d functioning as a stop shoulder for the tubing end, said tubing end is effectively connected to the connector 56 and thereby to the air outlet end of the squeeze bulb 16.

Now describing in detail the improved, simplified means provided by the herein invention for releasing air pressure assumed to have been previously supplied to the pneumatic cuff by hand squeeze applied to the bulb 16, reference is had to FIGS. 4 and 5, of which FIG. 4 illustrates said means being inactive because of the straightway extending relation of the tubing length portion in which said means if formed, whereas FIG. 5 illustrates the venting i.e. release of air in the tubing bore by simple thumb pressure applied to the outer tubing surface. More particularly, the tubing line 14 in a length portion thereof which is distal by a small amount from the connector 56, is provided with a transverse cut 26, made as by a razor blade or similar sharp bladed instrument, but which is not sufficiently deep as to extend entirely through the wall of the tubing to the tubing bore. Rather, according to the invention, communication between the tubing bore and the cut is established as by piercing the remaining wall portion disposed inwardly of the base line of the cut 26 with a hot needle or the like, such resulting in an air release or vent hole 28 being provided between the tubing bore and the cut.

Normally, however, both the cut 26 and to a lesser degree the hole 28 thereto are maintained closed to air flow outwardly therethrough by a multi-convolution, relatively stiff coil spring 30 of a length to extend along the tubing for an appreciable distance to both sides of said cut line 26 ad which has internal diameter slightly less than the external diameter of the tubing 14. Thus, when properly applied about the tubing the coil spring 30 maintains its position axially therealong by the slight inward compression which it exerts on the tubing external surface.

However, the stiffness of the coil spring 30, while being such as normally to maintain the length portion of the tubing which it encircles in straightway extending relation as in FIGS. 3 and 4, is not such as precludes bending of the tubing (here refer to FIG. 5) about the line of the transverse cut 26 provided therein as aforesaid, as by thumb pressure applied to said tubing and encircling spring just forwardly of said transverse cut 26. And when so slightly bent out of its normal straightway extending relation with respect to the extended axis of the squeeze bulb 16 and connector 56, air pressure in the tubing bore is released (vented) through the hole 28 and openedup transverse cut 26. If of course follows that upon release of thumb-pressure applied to the tubing as aforesaid, coil spring 30 functions to return the previously slightly bent length portion of the tubing to its normal straightway extending relation with respect to the extending axis of the squeeze bulb and connector 56, whereupon air pressure in the tubing line 14 may be reestablished or built up as needed.

Preferably, to insure that thumb pressure is applied to the external surfaces of the tubing and its encircling coil spring 30 which insures opening of the transverse cut 26, a marker 32 may be provided on the tubing surface just beyond the coil-spring end and at a point or small area on the tubing circumference which indicates to the user just where thumb pressure should be applied for best results.

Without further analysis, it will be appreciated that the herein invention provides a simple, effective means whereby with but slight bending of a length portion of the conventional tubing line extending between squeeze bulb and pneumatic cuff, deflation of the pneumatic cuff both delicately and under accurate control may be achieved and thus a patient's blood pressure may in turn be accurately recorded.

An understanding of the above and of the structure of the connector 56 will make it apparent that the tubing line may also be provided with the conventional manually operable valve means mounted in the connector. More particularly, FIGS. 3-5 inclusive show in broken lines one form of a conventional air release valve mounted in the connector interior space. Although not necessary or needed to effect release of the pneumatic cuff pressure, since the transverse cut 26 and vent hole 28 in the tubing wall, according to the present invention, suffices in this regard, the provision of the manually operable, conventional valve may serve to allow doctors, nurses, etc., to gradually become aware of and acquainted with the working of the pressure releasing means according to the invention, yet at the same time rely on the conventional manually operable valve during the interval usually required for such personnel to test to their own satisfaction the working of a novel, unorthodox (to them) means of deflating the pneumatic cuff.

As other embodiments of the invention may be possible of attainment. I do not limit myself to the precise constructional details of the pressure releasing means in a tubing line illustrated and described in the foregoing, but instead wish it understood that any and all such other embodiments which come within the scope of the appended Claims are to be considered as my invention.

I claim:

1. A sphygmomanometer including an inflatable-deflatable cuff, a pressure generating "squeeze" bulb, a tubing extending between said bulb and said cuff through the bore of which inflating air-pressure may be supplied to said cuff, means for effecting deflation of said cuff following inflation thereof as may be required in the taking of a patient's blood pressure, said means comprising a normally inactive, air-vent hold extending radically outwardly from the tubing bore through the tubing wall at a point along the length of said tubing proximal to said bulb, said air-vent hole being rendered active in response to limited bending pressure applied to the exterior surface of that portion of the tubing extending just beyond said hole in the direction of said cuff, and spring means operatively carried by said tubing length and extending axially therealong and to both sides of said hole for normally maintaining said tubing length portion in non-bent condition but permitting limited bending thereof as required to render said vent hole active.

2. A sphygmomanometer according to claim 1, wherein said means for effecting deflation of said cuff includes in addition to said air-vent hole, a transverse cut in the wall of said tubing disposed relatively radially outwardly of said hole and to the base line of which the hole opens, the construction and arrangement being such that slight bending of the tubing as aforesaid effects widening of the transverse cut and release of air pressure in the tubing bore through said hole and widened transverse cut, respectively.

3. A sphygmomanometer according to claim 1, wherein said spring means comprises a relatively stiff but bendable coil spring tightly encircling tubing length portions to both sides of said vent hole.

4. A sphygmomanometer accoring to claim 1, wherein said tubing is provided on its exterior surface with marking means indicative of the area of said exterior surface to which said limited bending pressure should be applied when bending of the tubing as aforesaid is desired.

5. A sphygmomanometer according to claim 1, wherein said tubing is connected to said squeeze bulb by means including a sleeve-form connector, and a manually operable air-releasing valve means is mounted in said connector, said valve means including operating means projecting from said connector.

* * * * *

UNITED STATES PATENT AND TRADEMARK OFFICE
CERTIFICATE OF CORRECTION

PATENT NO. : 4,142,518
DATED : March 6, 1979
INVENTOR(S) : WILLIAM L. HOWELL

It is certified that error appears in the above—identified patent and that said Letters Patent are hereby corrected as shown below:

Column 5, line 39, "hold" should read -- hole --.

Column 6, line 1, "radically" should read -- radially --.

Signed and Sealed this

Twenty-ninth Day of May 1979

[SEAL]

Attest:

RUTH C. MASON
Attesting Officer

DONALD W. BANNER
Commissioner of Patents and Trademarks